(12) United States Patent
Smith

(10) Patent No.: US 8,080,538 B2
(45) Date of Patent: Dec. 20, 2011

(54) METHOD FOR INCREASING ABSORPTION OF STEROID HORMONES

(76) Inventor: Edwin B. Smith, Pearland, TX (US)

( * ) Notice: Subject to any disclaimer, the term of this patent is extended or adjusted under 35 U.S.C. 154(b) by 1355 days.

(21) Appl. No.: 11/484,179

(22) Filed: Jul. 12, 2006

(65) Prior Publication Data

US 2008/0015171 A1    Jan. 17, 2008

(51) Int. Cl.
*A61K 31/56* (2006.01)
(52) U.S. Cl. .................................. 514/169; 514/171
(58) Field of Classification Search .................. 514/169, 514/171
See application file for complete search history.

(56) References Cited

U.S. PATENT DOCUMENTS

2006/0121103 A1*    6/2006    Kirby et al. .................. 424/449

* cited by examiner

*Primary Examiner* — Sreeni Padmanabhan
*Assistant Examiner* — Renee Claytor
(74) *Attorney, Agent, or Firm* — Edward E. Roberts; Howard Eisenberg

(57) ABSTRACT

Compositions and methods are disclosed wherein one or more steroid hormones are combined in a mixture with a sulfur-containing compound. The sulfur-containing compound increases the absorption of the steroid hormone through a mucosal surface, such as skin, oral mucosa, and mucosa of the gastrointestinal tract.

3 Claims, No Drawings

METHOD FOR INCREASING ABSORPTION OF STEROID HORMONES

CLAIM FOR BENEFIT OF EARLIER FILING DATE

The present utility application claims the benefit of U.S. Provisional Application No. 60/696,102 filed on May 7, 2005 and entitled "METHOD FOR INCREASING ABSORPTION OF STEROID HORMONES". The present utility application has the same inventor, subject matter and title as the aforesaid Provisional Application.

FIELD OF THE INVENTION

The invention pertains to the field of steroid hormones and particularly to the field of increasing the rate of absorption of steroid hormones through epithelial surfaces such as the skin and mucosal surfaces such as the oral mucosa.

DESCRIPTION OF THE INVENTION

In one embodiment, the invention is a composition for administration of a steroid hormone. According to this embodiment, the invention is a composition containing a steroid hormone and an amount of a sulfur-containing organic compound that is effective to increase the absorption of the steroid hormone through an epithelial surface of the body of a mammal.

The steroid hormone is preferably dehydroeipandrosterone (DHEA), pregnenolone, or a combination of DHEA and pregnenolone. However, it is conceived that the composition may contain other steroid hormones in addition to or instead of these two hormones.

The sulfur-containing organic compound may be, for example, a sulfonyl compound, a sulfonate compound, or a sulfhydryl compound (also referred to as a thiol or a mercaptan compound). A most preferred sulfur-containing organic compound for the composition of the invention is methyl ethyl sulfonate (MES). The composition of the invention may further contain other optional ingredients in addition to the steroid hormone and the sulfur-containing organic compound.

In another embodiment, the invention is a method for making a composition for administering a steroid hormone. According to this embodiment, a composition is made by combining, preferably by mixing, one or more steroid hormones and a sulfur-containing organic compound. Optionally, additional ingredients may be combined with the steroid hormone and the sulfur-containing organic compound.

According to this embodiment, the steroid hormone is preferably DHEA, pregnenolone, or a combination of DHEA and pregnenolone. However, it is conceived that other steroid hormones in addition to or instead of these two hormones may be combined with the sulfur-containing organic compound to make the composition. The sulfur-containing organic compound may be, for example, a sulfonyl compound, a sulfonate compound, or a sulfhydryl compound (also referred to as a thiol or a mercaptan compound). A most preferred sulfur-containing organic compound for the method of making a composition is MES.

In another embodiment, the invention is a method for increasing the absorption of a steroid hormone though an epithelial surface. According to this embodiment, the steroid hormone is combined with a sulfur-containing organic compound in an amount that increases absorption of a steroid hormone though an epithelial surface to make a composition and the composition is administered to an epithelial surface of a subject, such as a human subject.

The steroid hormone is preferably DHEA, pregnenolone, or a combination of DHEA and pregnenolone. The sulfur-containing organic compound is preferably a sulfonyl compound, a sulfonate compound, or a sulfhydryl compound (also referred to as a thiol or a mercaptan compound). A most preferred sulfur-containing organic compound for the method of making a composition is MES. The epithelial surface is preferably, the skin, the oral mucosa, or a mucosal surface of the gastrointestinal tract.

In another embodiment, the invention is a method for treating a medical condition that is ameliorated by treatment with a steroid hormone. According to this embodiment of the invention, a composition containing a steroid hormone and an effective amount of a sulfur-containing organic compound is administered to a subject in need thereof. It is conceived that the sulfur-containing organic compound increases the rate and/or the quantity of the steroid hormone that is absorbed into the body.

Preferably, the composition is administered by a route that permits absorption through the skin or through a mucosal surface. Thus, topical administration to the skin, such as by administration via a cream, a lotion, an ointment, or a transdermal patch, is one preferred route of administration. Topical administration to a mucosal surface is another preferred route of administration. The composition is then absorbed through the mucosal surface. Such administration is preferably through oral mucosa, such as by a lozenge or a gargle. Administration may also be oral with subsequent absorption through mucosal surfaces of the gastrointestinal tract. Such administration may be, for example, by a tablet, a capsule, a softgel (gel cap), or a liquid.

In this embodiment, the steroid hormone that is administered is preferably DHEA, pregnenolone, or a combination of DHEA and pregnenolone. The sulfur-containing organic compound may be, for example, a sulfonyl compound, a sulfonate compound, or a sulfhydryl compound (also referred to as a thiol or a mercaptan compound). A most preferred sulfur-containing organic compound for the method of administering a composition is MES. Conditions that may be treated by this method include any condition that is treatable by a steroid hormone, such as by DHEA, pregnenolone, or a combination of DHEA and pregnenolone. Many conditions have been reported to respond favorably to treatment with DHEA and/or pregnenolone.

The composition of the invention and the composition that is administered to a subject in need thereof may be a homeopathic composition, that is, a composition containing minute concentrations of DHEA and/or pregnenolone.

The invention is further illustrated below.

BACKGROUND

Steroidal hormones can be produced from a variety of tissues in the body. Steroidogenesis may be from adrenal, gonadal, and neural tissues and all have been derived from side-chain cleavage involving specific P 450 and non-P450 enzymes (7). DHEA (dehydroepiandrosterone) and pregnenolone are classified as steroid hormones naturally produced in the body (2). Production in a normal individual of DHEA is—females, 0.7 mg/day, and males, 3.0 mg/day. These are limiting values and are age related as there is no endogenous storage but are synthesized and available for immediate use by the body.

Essentially Pregnenolone and DHEA are one pass constituents in the blood. As shown below, the synthesis of cholesterol leads to the production of pregnenolone. The cholesterol is synthesized in the mitochondria (4) and requires NADP as a co-factor. Enzymes involved are the cytochrome P450 oxygenases found in mitochondria and zona reticularis, fasciculata, and glomerulosa. There are differences in the inner zones and outer zona glomerulosa enzymes. As shown, the cholesterol is first converted to pregnenolone and about half of this is metabolized to DHEA. To drive the production of DHEA, requires an excess of both. Both rapidly decline with age (1,2,3,4). These fat soluble steroids are lipid soluble molecules which, for the most part, penetrate cellular membranes by passive diffusion (2,7).

nenolone sulfate and with DHEA affects PMS and sexual arousal. The neurosteroidal activities are mediated by levels of circulating magnesium, and in some instances, zinc (8,9, 12), with stress altering or impairing the endoplasmic reticulum (ER) response to the state of the cell (9,10). The ER ensures cellular expression and is influenced by exogenous sources as to protein binding of the neurosteroids which effects treatments for seizures et al previously listed (11).

Homeopathic preparations of the DHEA/pregnenolone is important. Based on the Arndt Shultz Love of homeopathic treatment minute concentrations stimulate the desired reaction (5,6). The minute requirements concur with traditional

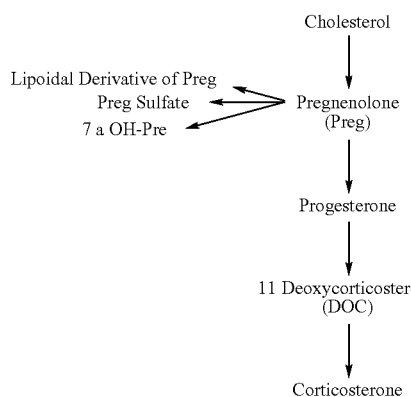
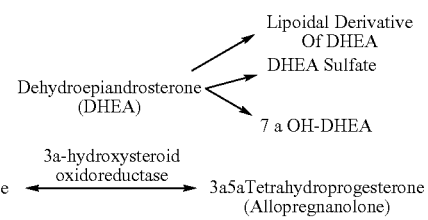

Anything which enhances the movement across skin to the circulatory system, which is sensitive to the domino effect, will effect transfer into the bloodstream. The DHEA/Pregnenolone circulate as the free form or as the DHEA-S in the blood and enter cells passively. To enhance the cascade effect and maximize the final results, an 80% DHEA/20% pregnenolone formulations (or variations thereof), in the presence of a sulfhydral compound for bonding and porosity control is optimally utilized. The DHEA/pregnenolone are optimally absorbed through the skin and into the bloodstream.

DHEA has been shown to have a function in cancer prevention, arterial disease, multiple sclerosis, Alzheimer's disease, and may be beneficial in treating lupus, osteoporosis, immune system activity, and memory. Pregnenolone can be metabolized from cholesterol into a variety of other hormones including DHEA, progesterone, testosterone, and estrogen. Pregnenolone supplements have shown to beneficially treat symptoms (1,2) and also lower the circulating cholesterol levels, and alleviate symptoms of Alzheimer's, lupus, multiple sclerosis, PMS, rheumatoid arthritis, scleroderma, seizures, psoriasis, prostate disorders, stress, trauma, injuries, sleep disorders, and chronic fatigue syndrome.

In conjunction with pregnenolone, hormone replacement therapy effectiveness is enhanced with a concomitant improvement in the immune system (1,2,3). Low levels of DHEA are associated with diabetes, lupus, male sexual dysfunction, and prostate disorders, clinical mental depression, asthma, osteoporosis, and depressed immunity. Literature has also shown that DHEA and/or pregnenolone enhance athletic performance, impotence, depression, menopause, osteoporosis, atherosclerosis, and hypertension.

Neurosteroids regardless of source within the body function in neural tissue by ion channel receptors GABA, NMDA, and other amino acid ones (7). Stress activates the GABA receptor and also Pregnenolone sulfate which have been associated with seizure disorders. Memory is improved by Pregnenolone sulfate and with DHEA affects PMS and sexual medicine (7) and homeopathic medicine low concentrations working naturally and gently in the body.

The inversion of GABA, modulated DHEA/pregnenolone sulfate plasma concentrations is associated with estrogenic cycle induced migraines and/or PMS cycling (7). The low levels from the homeopathic liquid which retains memory, and contains sufficient ability to be absorbed transmucosal and blood/brain to function in the treatment (6).

CLAIMS

1. Enhancement of sublingual, oral, and skin absorption of the DHEA/pregnenolone into the blood circulation by a unique delivery system in a carrier.
2. Depression of intracellular histamine and other antioxidants.
3. Improved oxidation through the ETS with increased energy from FAD, NADP, NAD for intracellular use.
4. Depressed levels of cortisol from forcing the pathway toward the sex hormones.
5. Reduce the severity and alleviate the incidence of menstrual cramps.
6. Alleviation of the symptoms of migraines.
7. A homeopathic version of 10X has been shown to be equally effective.

ETS=Electron Transport System
FAD=Flavine Adenine Diphosphate
NADP=Nicotine Adenine Triphosphate
NAD=Nicotine Adenine Diphosphate

SUMMARY

A new and novel method of facilitating membrane transport of the steroids DHEA/Pregnenolone through and into the bloodstream. The levels of DHEA/Pregnenolone and relationship thereof improve the ability to absorb, in conjunction with a sulfur compound such as sulfonate, and to drive the pathway in such a way as to enhance steroid circulatory level. This enhanced level of DHEA/Pregnenolone reduces histamine levels associated with migraines and cortisol, while increasing the oxidative benefits intracellularly. The method of the invention in supplying the DHEA/pregnenolone either conventionally or homeopathic was effective.

EXAMPLES

Three forms of the formulation were developed. The sublingual variations are as follows:

| Sublingual | Quantity/liter | Range |
|---|---|---|
| DHEA, g | 80.0 | 0-200 |
| Lo Han Kuo, g (Splenda) | 33.33 (TBD) | 0-100 (0-25) |
| Pregnenolone, g | 20.0 | 0-200 |
| T-20, ml | 1.0 | 0-5 |
| Ethanol, ml | 400.0 | 0-600 |
| Glycerine, ml | 380.0 | 0-500 |
| Water, ml | 100.0 | 0-500 |
| Propylene Glycol, ml | 50.0 | 0-500 |
| Methyl Ethyl Sulfonate (MES), ml | 0.5 | 0.05-5.0 |
| Cinnamon Oil, ml (any flavoring) | 0.5 | 0.05-5.0 |
| Myristic Acid Ethoxylate, ml | 70.0 | 0-200 |
| Magnesium Molybdate, g | 3.2 | 0-40 |
| Zinc Sulfate 7 $H_2O$, g | 0.412 | 0-25 |

1. Mix DHEA in 200 ml alcohol.
2. Mix pregnenolone in 200 ml alcohol+T-20+glycerine+Propylene glycol+MES+Cinnamon oil+myristic acid.
3. Mix remaining items (magnesium and zinc) in water.
4. Combine all premixes after mixing thoroughly.

Gel Cap Formulation

| | Quantity/Liter | Range |
|---|---|---|
| DHEA, g | 80.0 | 0-200 |
| Pregnenolone, g | 20.0 | 0-200 |
| T-20, ml | 1.0 | 0-10 |
| Olive Oil, ml | 660.0 | 0-800 |
| Glycerine, ml | 200.0 | 0-800 |
| Cinnamon Oil, ml | 0.5 | 0.05-5.0 |
| MES, ml | 0.5 | 0.05-10.0 |
| Propylene Glycol, ml | 50.0 | 0-200 |
| Vitamin E, ml | 5.0 | 0-25 |

Mix in one batch, assuring that no particulates remain.

Skin Creme

| Part A: | 67% | Isopropyl myristate | 50-80 (Range) |
|---|---|---|---|
| | 8% | Palmitic Acid | 0-25 |
| | 3.2 g | DHEA | 0.8-20 |
| | 0.8 g | Pregnenolone | 0.1-10 |
| Part B: | 22% | Water | 10-50 |
| | 3% | Triethanolamine | 1-10 |
| | 0.5% | Magnesium oxide | 0-25 |
| | 0.05% | Zinc oxide | 0-5 |

1. Heat Parts A and B to 75 degrees Celsius.
2. Add Part B to Part A with continual mixing.
3. Add with mixing Propylene Glycol 0.1% (0.01-20.0)

MES 0.1% (0.01-3.0)
Odorant 0.1% (0.01-5.0)
4. Optional—Trimethyl glycine 0.005% (0.001-10.0)

Homepathic Version

| Base | Quantity/l | Range |
|---|---|---|
| Ethanol, ml | 400.0 | 0-600 |
| Glycerine, ml | 250.0 | 0-500 |
| Propylene Glycol, ml | 46.0 | 0-500 |
| T-20, ml | 2.0 | 0-10 |
| Brij 35, g | 1.0 | 0-10 |
| MES, ml | 0.5 | 0.05-5.0 |
| Cinnamon Oil (Flavoring), ml | 0.5 | 0.05-5.0 |
| Water, ml | 100.0 | 0-500 |
| Magnesium Molybdate, g | 0.32 | 0-40 |
| Zinc Sulfate, g | 0.04 | 0-25 |

1X Version
1. Mix 80 g DHEA in 200 mls Ethanol.
2. Mix 20 g Pregnenolone in remaining alcohol+T-20+Glycerine+Propylene glycol+MES+Cinnamon Oil+Brij 35.
3. Add magnesium molybdate, zinc sulfate to water.
4. Add 1 and 2 to 3.
5. Succuse 100 times—this is 1X Version.

Base Mix
1. Mix Brij 35 into ethanol—totally dissolve.
2. Mix magnesium molybdate and zinc sulfate into water.
3. In sequence, add components into ethanol and then add water solution.

1X Version
9 Parts Base containing 1 part 80:20 DHEA/Pregnenolone

2X Version
9 Parts Base+1 part 1X Version, succuse 100 times.

3X Version
9 Parts Base+1 part 2X Version, succuse 100 times.

Results

Preliminary data on a limited number of individuals has shown no difference due to type of formulation or routes of administration. All have caused the desired effects. Ten individuals suffering from recurring migraine headaches received the proposed formulations. Based on the results obtained, if the treatment began at symptom inception, each formulation was equally successful in alleviating migraine pain. This mechanism of action is modulated by the Electron Transport System (ETS), and results in reduced histamine and increased energy forms.

Through the enhanced level of female and male sex hormones and the lowering of histamine levels, the formulations were able to reduce the severity and rapidly alleviate (usually within five minutes) the incidence and severity of the menstrual cramps. Five women who complained of severe menstrual cramping and sometimes missed work due to severity of menstrual cramps were given the three formulations with spectacular results. Within five minutes of application, the severity and incidence of the menstrual cramps were significantly decreased.

A homeopathic version of the sublingual (10X) was found to be as effective on four women (individuals remaining from the previous study). 3X was tested in 10 women and found to be effective on migraines. Because of the small dose of active ingredients, the potential effect of the active ingredients—DHEA/Pregnenolone—is unknown from the literature.

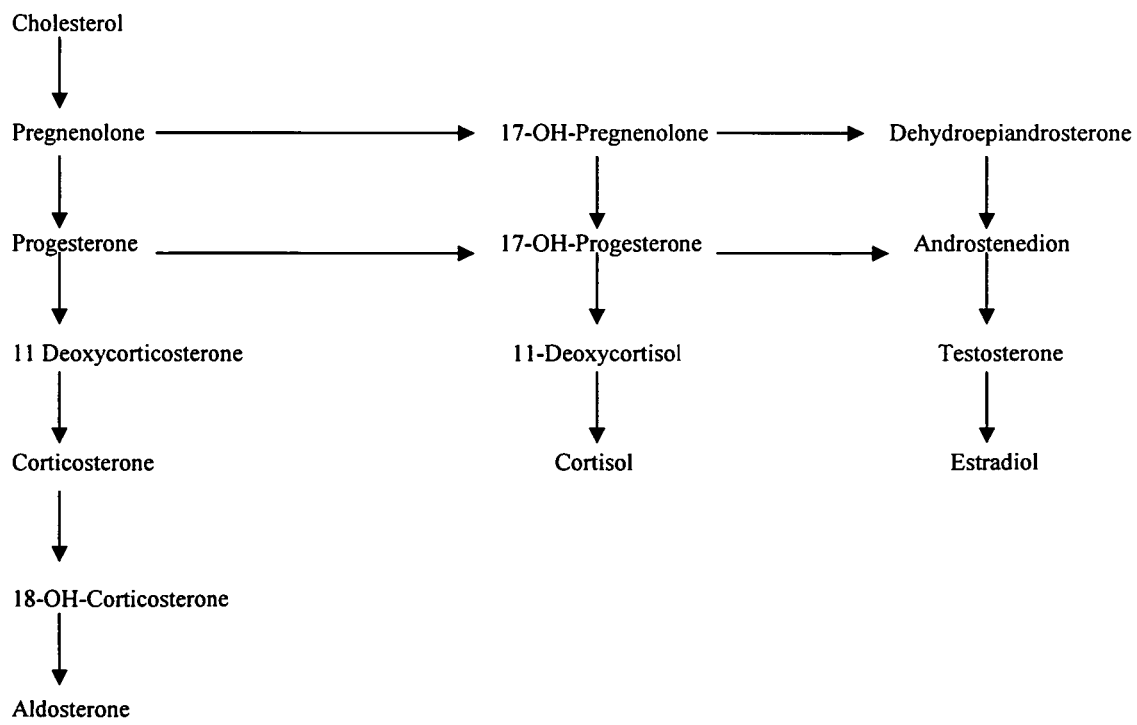

The use of the neurosteroids DHEA and Pregnenolone individually as medical substances and nutritional supplements has been widely studied and documented. The use of these cholesterol derived steroids orally, injected, and with other avenues of administration, and in conjunction with other substances is well known. DHEA effects are on athletic performance, impotence, depression, whereas pregnenolone affects menopause, impotence, and osteoporosis, among other things. Transport across the membranes of the body of lipid soluble substances by DMSO is well known. The approach used here is to use a methyl ethyl sulfonate and longer chains of sulfonates and mineral sulfonates, which are not as effective, to increase pore size and enhance active or passive transport. The cascade effect of the enhanced absorption of the DHEA/pregnenolone induced enables the levels in the blood and cells to be increased. The increased or enhanced levels of the steroids reduce histamine levels associated with migraines. Cortisol is also reduced. The reduction in histamine causes a concomitant increase in the ETS produced energy compounds. Because of the extremely low levels of the DHEA/pregnenolone required for action, all forms of supply worked—sublingual, oral, skin creme, and homeopathic variants.

What is claimed is:

1. A method for increasing the absorbability of a steroid hormone through an epithelial surface comprising combining in a composition a steroid hormone and methyl ethyl sulfonate in an amount that increases the absorption of the steroid hormone through an epithelial surface.

2. A method for making a composition comprising mixing a steroid hormone with methyl ethyl sulfonate to obtain a mixture, wherein the concentration of methyl ethyl sulfonate is in an amount sufficient to increase the absorption of the steroid hormone through an epithelial surface of a mammal.

3. The method of claim 2 wherein the steroid hormone is dehydroepiandrosterone, pregnenolone, or a combination of dehydroepiandrosterone and pregnenolone.

* * * * *